United States Patent [19]
Blair et al.

[11] Patent Number: 6,076,406
[45] Date of Patent: Jun. 20, 2000

[54] INTEGRATED SENSING PLATFORM AND METHOD FOR IMPROVED QUANTITATIVE AND SELECTIVE MONITORING OF CHEMICAL ANALYTES IN BOTH LIQUID AND GAS PHASE

[75] Inventors: Dianna S. Blair, Albuquerque; Gregory C. Frye-Mason, Cedar Crest; Michael A. Butler, Albuquerque, all of N. Mex.

[73] Assignee: Sandia Corporation, Albuquerque, N. Mex.

[21] Appl. No.: 09/048,237

[22] Filed: Mar. 25, 1998

[51] Int. Cl.[7] .................................................. G01H 3/00

[52] U.S. Cl. ..................... 73/590; 73/19.03; 73/24.06; 73/61.61

[58] Field of Search ................................. 73/19.03, 24.01, 73/24.03, 24.04, 24.06, 61.41, 61.61, 590, 597, 599, 23.34, 31.02, 31.01, 31.03; 422/90, 91

[56] References Cited

U.S. PATENT DOCUMENTS

| | | | |
|---|---|---|---|
| 4,020,830 | 5/1977 | Johnson et al. | 128/2 E |
| 4,055,072 | 10/1977 | Fletcher et al. | . |
| 4,225,410 | 9/1980 | Pace | 204/195 R |
| 4,312,228 | 1/1982 | Wohltjen | . |
| 5,076,094 | 12/1991 | Frye et al. | . |
| 5,442,169 | 8/1995 | Kunz | 250/227.21 |
| 5,482,678 | 1/1996 | Sittler | 422/90 |

*Primary Examiner*—Hezron Williams
*Assistant Examiner*—Thuy Vinh Tran
*Attorney, Agent, or Firm*—Russell D. Elliott

[57] ABSTRACT

By measuring two or more physical parameters of a thin sensing film which are altered when exposed to chemicals, more effective discrimination between chemicals can be achieved. In using more than one sensor, the sensors are preferably integrated on the same substrate so that they may measure the same thin film. Even more preferably, the sensors are provided orthogonal to one another so that they may measure the same portion of the thin film. These provisions reduce problems in discrimination arising from variations in thin films.

11 Claims, 3 Drawing Sheets

INTEGRATED SENSING PLATFORM AND METHOD FOR IMPROVED QUANTITATIVE AND SELECTIVE MONITORING OF CHEMICAL ANALYTES IN BOTH LIQUID AND GAS PHASE

This invention was made with support from the United States Government under Contract DE-AC04-94AL85000 awarded by the U.S. Department of Energy. The Government has certain rights in this invention.

FIELD OF THE INVENTION

The present invention is directed to a method and device for determining concentrations and/or identities of compounds. In particular, the present invention is directed to using thin sensing films having physical properties which are altered when exposed to chemical analytes. Further, the invention is directed to incorporating the use of multiple sensors capable of sensing different film properties which undergo simultaneous (or nearly simultaneous) alteration upon exposure of the film to chemical analytes.

BACKGROUND OF THE INVENTION

Many current sensing platforms use thin films made of membranes, polymers, solgels, etc., to determine identity and/or concentration of analytes of concern. These thin film technologies have inherent limitations with regard to selectivity. In particular, the thin films are not analyte specific. Therefore, the sensors incorporating such thin films respond to classes of compounds in the same manner. No additional specific information is provided by the transduction mechanism of these thin films.

Thus, concentrations are often reported as equivalent values, where a specific concentration is assumed to be of a particular compound. For example, all aromatic organic compounds are often reported as "toluene equivalent" concentrations. For some compounds, this equivalent is a fairly accurate representation of the concentration of the analyte, while for other compounds, it can be inaccurate by an order of magnitude or more.

In order to improve the discrimination ability of the current sensor technologies, one proposed solution has been to use arrays of sensors where multiple devices of the same sensor type are coated with different thin films. However, the information provided by each individual sensor is not unique when compared to the response of the other sensors. In other words, the information provided by additional sensors represents an incremental increase over the information provided by all previous sensors. Building a calibration model based on the response signal from all of the sensors after exposure to a particular analyte improves the overall selectivity of the sensing system, but also is very difficult. Further, the potential for failure of this sensing system goes up geometrically in accordance with the number of individual sensors in the array.

In order to obtain high selectivity using multiple devices with different thin films, a large array of sensors is required. This poses a problem with respect to fabrication and calibration, as well as long term stability and use. It is difficult to cast equivalent and reproducible films, especially at a reasonable cost.

SUMMARY OF THE INVENTION

Therefore, it is an object of the present invention to provide necessary speciation and quantitation of gas and liquid phase analytes while limiting the number of devices required to accomplish this end. In doing so, manufacturing cost is reduced and useful lifetimes of the sensors are improved. It is a further object of the present invention to exploit the fact that more than one physical parameter of thin sensing films is altered and detectable when the films are exposed to chemical analytes.

These and other objects of the present invention are fulfilled by providing an integrated sensing platform having 1) at least one thin film which reacts when exposed to chemicals, and 2) at least two different sensors, or transduction mechanisms, which detect at least two different physical properties of the thin film.

The sensors may be positioned orthogonally to one another or otherwise such that they do not interfere with one another. In this way, they may even be positioned to sense the same portion of a thin film. The properties to be detected by the sensors may include mechanical, optical, or electrical properties. By way of illustration, a suitably detectable mechanical property can be mass, a suitable optical property can be refractive index, and a suitable electrical property can be dielectric constant. A sensing platform made according to the principles of the invention could, for instance, include a surface acoustic wave detector together with an optical refractive index detector. Surface acoustic wave (or SAW) devices are capable of identifying and quantifying absorbed chemical species by measuring changes in velocity and attenuation of an acoustic wave traveling through a thin film onto which the chemical species is sorbed. U.S. Pat. No. 4,055,072 (Fletcher), U.S. Pat. No. 4,312,228 (Wohltjen) and U.S. Pat. No. 5,076,094 (Frye, et al.) describe aspects of SAW technology and are hereby incorporated by reference in their entirety. Although the apparatus of the present invention will function with only two sensors, it is possible and perhaps desirable to include more sensors to achieve greater output or enhanced performance; for example, inclusion of a third sensor for sensing a third property, which is different from the other properties detected with respect to the thin film, may likewise be integrated on the substrate.

The objects of the present invention are also fulfilled by providing a method of discriminating chemical compounds based on their identity or concentration. This is accomplished by simultaneously considering sensor data from at least two different sensors selected and designed to monitor different physical parameters of a thin film after it has been exposed to an analyte.

Multiple sensors may be used to detect changes in a single film, and, as suggested above, they can even be deployed to sense changes over the same portion of a given film.

The objects of the present invention are also realized by the method disclosed here for performing integrated sensing including the steps of providing on a substrate a thin film having physical parameters which change when the film is exposed to analyte chemicals, providing on the substrate at least two sensors capable of sensing at least two different parameters of the thin film, and collecting and analyzing sensor data following exposure of the film to one or more analyte chemicals so as to permit differentiation with regard to species or concentration of the one or more analyte chemicals.

Further scope of the applicability of the present invention will become apparent from the detailed description given below. However, it should be understood that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description and the accompanying drawings which are given by way of illustration only, and thus are not limited to the present invention, and wherein.

DETAILED DESCRIPTION OF THE PREFERRED EMBODIMENT

Figure 1:
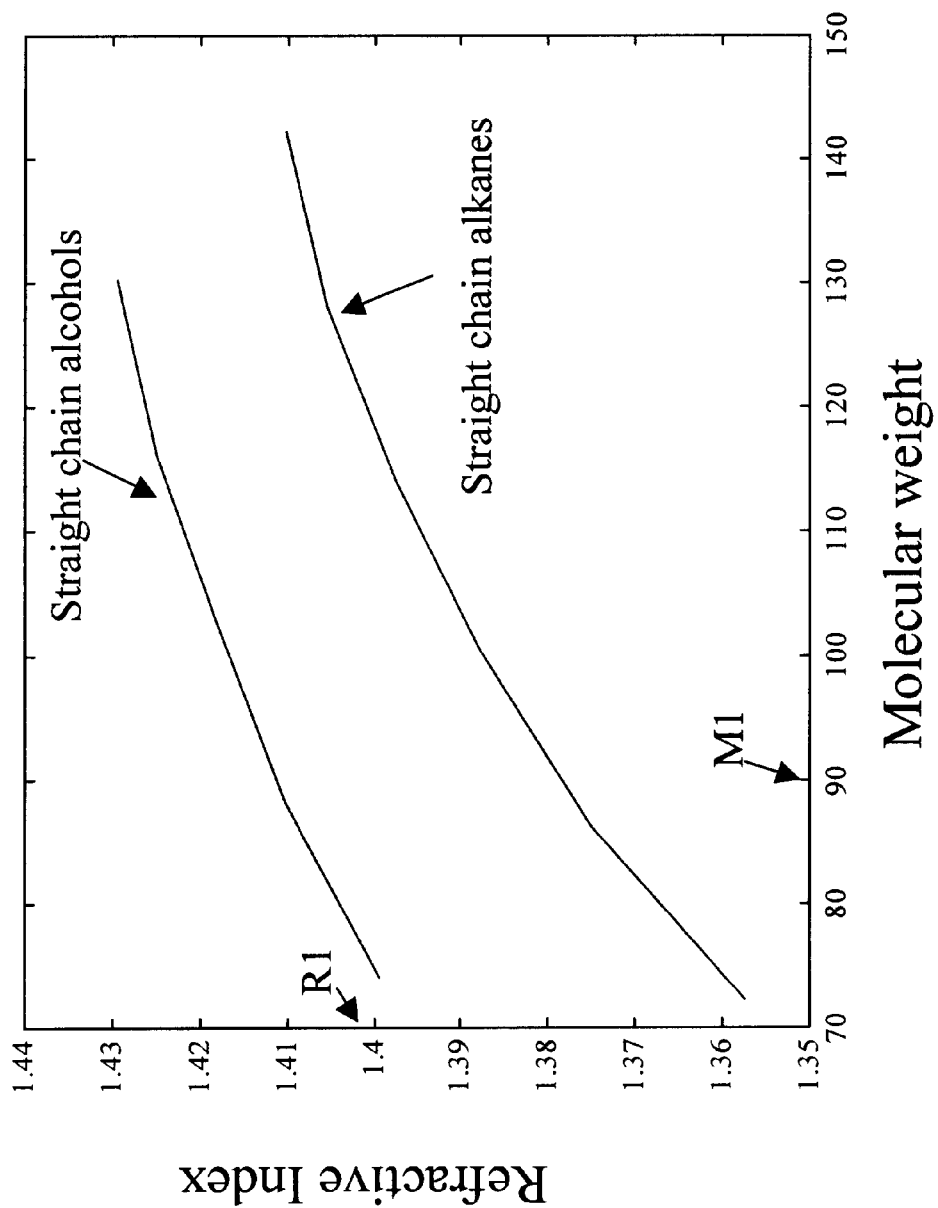
FIG. 1 is a plot illustrating the benefit of multiple sensors in the context of the invention.

FIG. 1 illustrates that in attempting to distinguish chemical analytes based on their measurable physical characteristics, it is often beneficial to measure two or more properties rather than simply one. Information that follows adheres to established principles of multivariate analysis.

Shown in FIG. 1 are data which hypothetically could be collected using a Mach-Zehnder interferometer and a surface acoustic wave device. The data depicted are for refractive index (RI) and molecular weight (MW) associated with two classes of analyte compounds: straight chain alcohols and straight chain alkanes. Because of the variability in both size and optical characteristics of different molecules within each category, a range of values for both RI and MW could be measured.

As between the alcohols and the alkanes, overlaps may be observed with respect to both RI and MW data. For example, molecules from both analyte categories can be detected which have molecular weights in the range of 80 to 125. Therefore, where the MW data fall within that range, there was no way to distinguish the alcohols from the alkanes strictly on the basis of molecular weight. Likewise, a RI of slightly greater than 1.4 might be measured for samples of both the alcohol and the alkane species. Without more information, the two categories of compounds are indistinguishable on the basis of RI, at least where the measured values overlap.

FIG. 1, however, illustrates that when the two sets of values are plotted on a cartesian coordinate system, data for the straight chain alcohols (represented by a solid line in the graph) are easily distinguishable from data for the straight chain alkanes (represented by a dashed line). It is this principle that underlies the concept of integrating multiple detection instrumentalities on a single platform to assist in discriminating between chemical analytes.

The simple example shown in FIG. 1 disregards any analyte concentration effects that would be exhibited in both mass and refractive index changes. This can further confound conclusions made from univariate measurement. However, if both the mass and the refractive index are being monitored, changes in both of these film properties may be used to uniquely identify an analyte. Thus, use of this information simultaneously allows greater speciation than the individual technologies alone can provide. The increased speciation provided by considering more than one feature at a time reduces the number of devices required to provide a desired selectivity.

Figure 2:
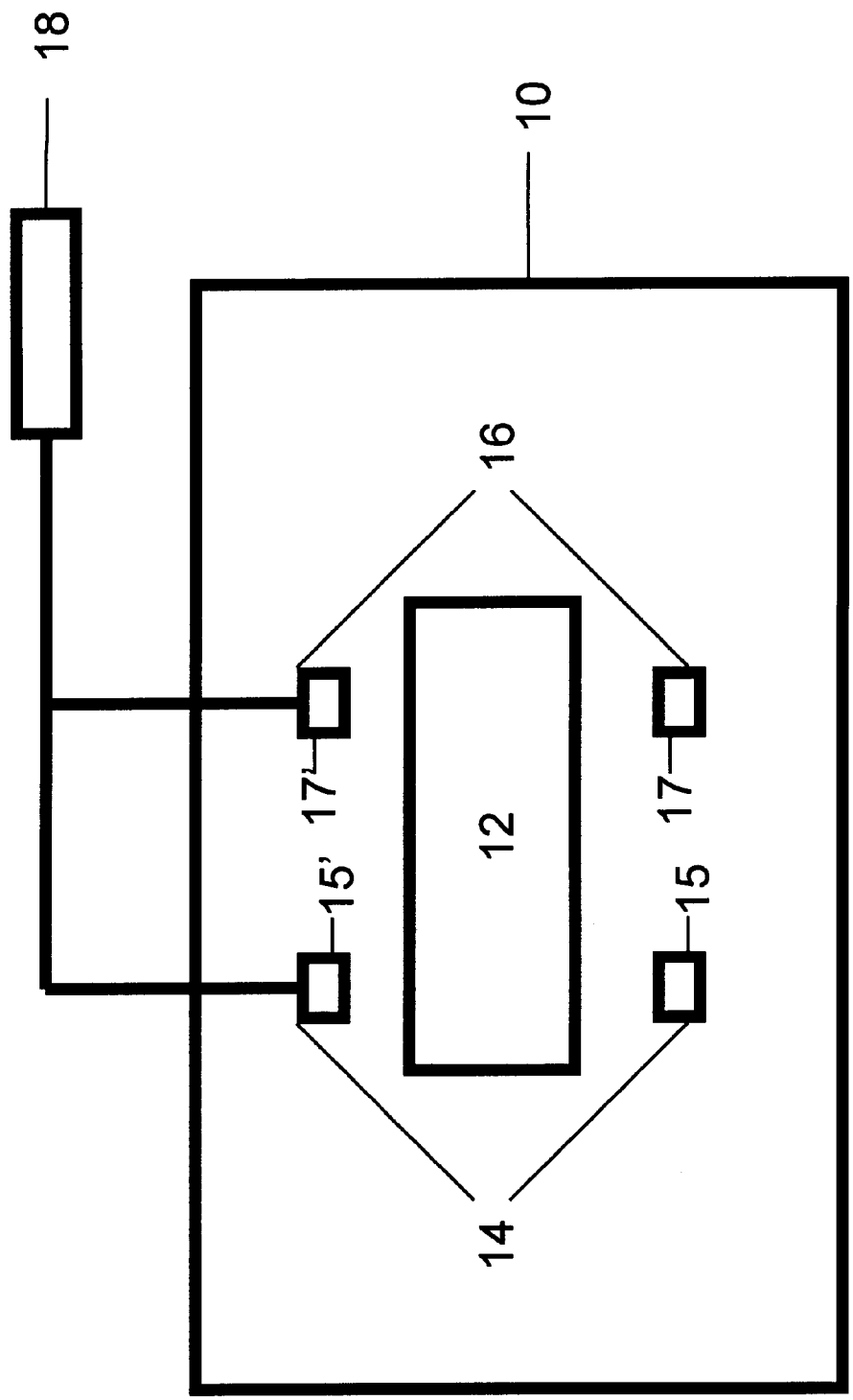
FIG. 2 is a schematic view of an integrated sensing platform according to the present invention.
Figure 3:
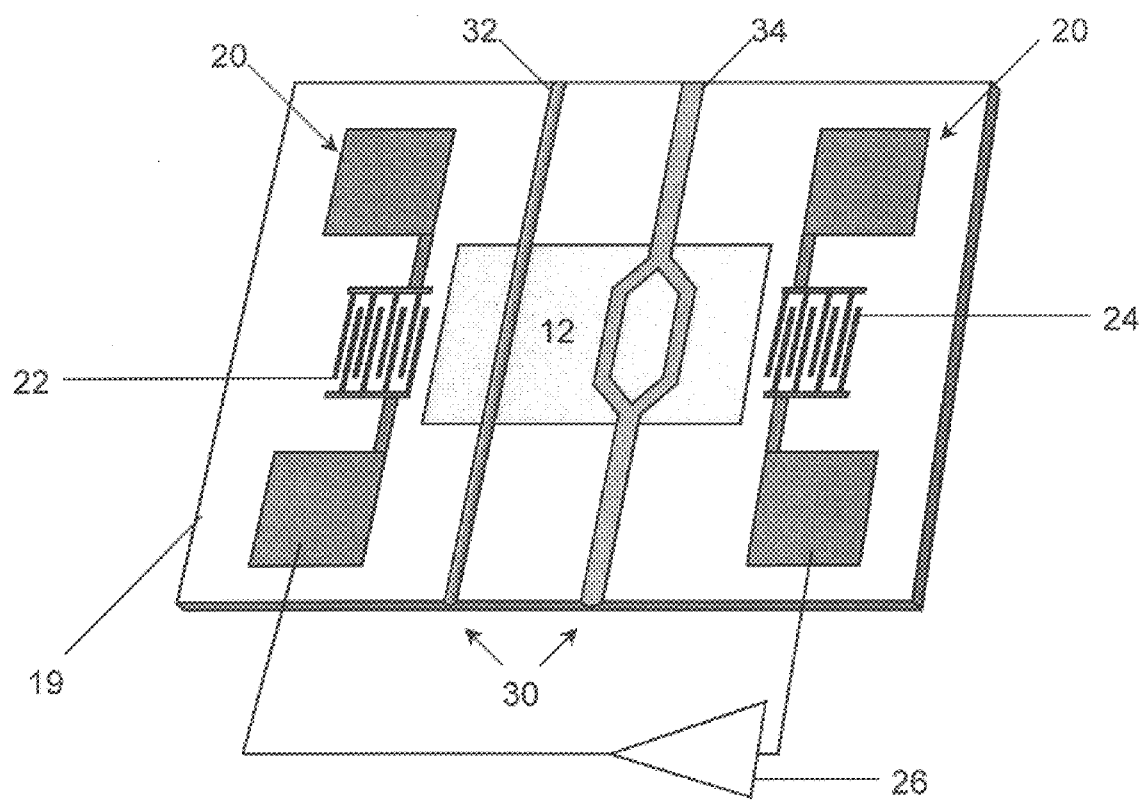
FIG. 3 is a top elevational view of a more detailed embodiment of the present invention.

In measuring more than one parameter of the thin film, it is advantageous to integrate the sensors on the same platform so that they measure the same thin film. This integration reduces problems in discrimination arising from variations in thin films being monitored by different sensors. As shown in FIGS. 2 and 3, two sensors which measure different physical parameters are provided adjacent to one another (arranged parallel to each other, orthogonal to each other, or otherwise so that they do not interfere with each other) and sense different properties of the same thin sensing film.

FIG. 2 depicts schematically a simple integrated sensing platform 1 illustrating principles of the present invention. The platform 1 includes a thin sensing film 12, a first sensor 14 and a second sensor 16. For purposes of the illustration in this figure, assume the sensors are acoustic or optical sensors, and, consistent with this assumption, the first sensor comprises a source 15 and a detector 15', and the second sensor likewise comprises a source 17 and a detector 17'. As indicated throughout this disclosure, other types of sensors which may or may not include a source and detector are contemplated by the invention. The choice sensors for this illustration are not intended to be limiting on the scope of the claimed invention as a whole. Referring to the figure, the thin sensing film 12, the first sensor 14, and the second sensor 16 are all integrated on a substrate 10. In the embodiment shown in FIG. 2, the sensors are positioned substantially parallel to one another, and the sensors 14 and 16 target the same thin film. They do not, however, in this illustration, obtain measurements from the same part of the thin film 12. (There is likely to be some degree of uniformity in response to an analyte over different parts of a given thin film. For certain applications, though, it may be desirable for a plurality of sensors to obtain measurements across, as nearly as is practical, the same portion of the thin film. This is discussed in more detail below in connection with FIG. 3.)

The thin sensing film 12 acts as a medium for providing information useful in determining concentration or identity of an analyte which is either in a liquid phase or a gas phase. Properties associated with the thin sensing film 12 change after it has been exposed to chemical analytes. The two sensors 14 and 16 measure different properties of the thin film 12 that are affected by exposure of the film 12 to chemical analytes. As discussed above in reference to FIG. 1, the combination of information gathered by both sensors is in certain circumstances more useful than information from either sensor, separately, in distinguishing speciation or concentration of analytes.

Measurement outputs from the sensors 14, 16 are supplied to a processor 18, which may be (but need not be) integrated on the substrate 10. The processor performs the discrimination between chemical compounds according to the principles of multivariate analysis using data obtained from the two sensors 14 and 16. Results of the analysis performed by the processor 18 may be retrieved according to any desired format which is suited to the processor.

In a detailed preferred embodiment shown in FIG. 3, sensors 20, 30 are positioned orthogonally to one another on a substrate 19 so that the sensors not only sense the same thin sensing film 12 positioned on the substrate 19, but indeed they sense the same area of the thin sensing film 12. In an actual integrated sensing platform made according to the principles of this invention, the sensors need not be positioned precisely orthogonally, so long as they do not interfere with each other. Measuring of the same portion further reduces risk that accuracy of the integrated sensors may be diminished due to variations across the area of the thin sensing film 12.

In this embodiment, a surface acoustic wave (SAW) detector 20 examines changes in mass and viscoelastic properties of the thin sensing film 12 after it has been exposed to chemical analytes. An optical refractive index (ORI) sensor 30 simultaneously (or nearly simultaneously) provides information about changes in the real and imaginary portions of the refractive index of the film 12. The SAW element 20 is constructed in a conventional manner and includes an input interdigital transducer 22, an output interdigital transducer 24 and an amplifier 26 electrically connected therebetween. A piezoelectric material suitable for forming an acoustic device, such as lithium niobate, is the material used for the substrate 19. The thin sensing film 12 is provided between the transducers 22, 24.

The ORI sensor includes a straight wave guide 32 and an interferometric wave guide 34 provided between the thin sensing film 12 and the substrate 19. The straight wave guide 32 provides information about the optical absorption or the imaginary part of the refractive index of the thin sensing film 12. The interferometric wave guide 34, shown as a Mach-Zehnder interferometer, provides information about the real portion of the refractive index of the thin sensing film 12.

Data such as those shown in FIG. 1 may be obtained using the particular configuration shown in FIG. 3. As noted above, while neither ORI (supplying RI data) nor SAW (supplying MW data) alone are capable of providing sufficient discrimination between long chain alcohols and long chain alkanes, the different analytes can be distinguished by considering the data from both sensors.

In addition to the integration of two different types of sensors on a single platform for the simultaneous or near simultaneous use of different physical parameter measurements in discriminating between chemical compounds, a third and possibly more properties of the thin film can be measured and analyzed. The additional data can be analyzed according to multivariate analysis principles, and likewise plotted on a multiple axis Cartesian coordinate system to aid in distinguishing analytes. In this way, the number of discrete elements needed to provide adequate speciation is reduced. An example of a third measurable property is the dielectric constant of the thin sensing film. Other means for measuring properties of thin films which are affected by exposure to chemical analytes are known to those skilled in the art, and can be incorporated into the integrated sensing platform of the present invention without departing from the scope and spirit of the appended claims.

The integrated sensors may also be provided in arrays using different thin sensing films on each integrated sensor. This would provide additional information to aid in discrimination. An array of integrated sensors would require fewer elements than an array of individual sensors measuring a single parameter for the same level of speciation.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. An integrated sensor comprising:
   a thin film which reacts when exposed to chemicals;
   a first sensor sensing a first property of said thin film; and
   a second sensor sensing a second property, different from said first property, of said thin film,
   wherein said thin film, said first sensor and said second sensor are integrated on a substrate.

2. The sensor of claim 1, wherein said first sensor and said second sensor are positioned orthogonally to one another.

3. The sensor according to claim 1, wherein said first sensor and said second sensor sense a same portion of said thin film.

4. The sensor according to claim 1, wherein said first property is a mechanical property and said second property is an optical property.

5. The sensor according to claim 4, wherein said first sensor is a surface acoustic wave detector and said second sensor is an optical refractive index detector.

6. The sensor of claim 1, further comprising a third sensor integrated on the substrate, said third sensor sensing a third property of said thin film, said third property being different from said first property and said second property.

7. The sensor according to claim 6, wherein said first property is a mechanical property, said second property is an optical property, and said third property is an electrical property.

8. A method of forming an integrated sensor comprising:
   providing a thin film on a substrate, the thin film having physical parameters which change when exposed to chemicals;
   providing a first sensor on the substrate, the first sensor, measuring a first parameter of the thin film; and
   providing a second sensor on the substrate, the second sensor measuring a second parameter of the thin film, said second parameter being different from said first parameter.

9. The method of claim 8, further comprising providing the first sensor and the second sensor orthogonally to one another.

10. The method of claim 8, further comprising providing further sensors for measuring further parameters of the thin film, the further parameters being different than said first and second parameters.

11. A method of multivariate analysis comprising the step of:
   collecting data using a sensor selected from the group consisting of
   an integrated sensor comprising:
      a thin film which reacts when exposed to chemicals,
      a first sensor sensing a first property of said thin film, and
      a second sensor sensing a second property, different from said first property, of said thin film,
      wherein said thin film, said first sensor and said second sensor are integrated on a substrate;
   an integrated sensor comprising:
      a thin film which reacts when exposed to chemicals,
      a first sensor sensing a first property of said thin film, and
      a second sensor sensing a second property, different from said first property, of said thin film,
      wherein said thin film, said first sensor and said second sensor are integrated on a substrate, and wherein said first sensor and said second sensor are positioned orthogonally to one another,
   an integrated sensor comprising:
      a thin film which reacts when exposed to chemicals,
      a first sensor sensing a first property of said thin film, and
      a second sensor sensing a second property, different from said first property, of said thin film,
      wherein said thin film, said first sensor and said second sensor are integrated on a substrate, and wherein said first sensor and said second sensor sense a same portion of said thin film, an integrated sensor comprising:
   a thin film which reacts when exposed to chemicals,
   a first sensor sensing a first property of said thin film, and
   a second sensor sensing a second property, different from said first property, of said thin film,
   wherein said thin film, said first sensor and said second sensor are integrated on a substrate, and wherein said first property is a mechanical property and said second property is an optical property;

an integrated sensor comprising:
   a thin film which reacts when exposed to chemicals,
   a first sensor sensing a first property of said thin film, and
   a second sensor sensing a second property, different from said first property, of said thin film,
   wherein said thin film, said first sensor and said second sensor are integrated on a substrate, and wherein said first sensor is a surface acoustic wave detector and said second sensor is an optical refractive index detector;

an integrated sensor comprising:
   a thin film which reacts when exposed to chemicals,
   a first sensor sensing a first property of said thin film, and
   a second sensor sensing a second property, different from said first property, of said thin film,
   wherein said thin film, said first sensor and said second sensor are integrated on a substrate,
   and further comprising a third sensor integrated on the substrate, said third sensor sensing a third property of said thin film, said third property being different from said first property and said second property;

an integrated sensor comprising:
   a thin film which reacts when exposed to chemicals,
   a first sensor sensing a first property of said thin film, and
   a second sensor sensing a second property, different from said first property, of said thin film,
   wherein said thin film, said first sensor and said second sensor are integrated on a substrate,
   and further comprising a third sensor integrated on the substrate, said third sensor sensing a third property of said thin film, said third property being different from said first property and said second property,
   wherein said first property is a mechanical property, said second property is an optical property, and said third property is an electrical property;

and any combination thereof.

* * * * *